(12) United States Patent
Mann et al.

(10) Patent No.: US 9,874,516 B2
(45) Date of Patent: *Jan. 23, 2018

(54) DETECTION SYSTEM AND METHOD OF DETECTING CORROSION UNDER AN OUTER PROTECTIVE LAYER

(71) Applicant: SubTeraNDT Limited, Carlow (IE)

(72) Inventors: Christopher Mark Mann, Cornwall (GB); Joseph Peter Dunne, Carlow (IE)

(73) Assignee: SubTeraNDT Limited, Carlow (IE)

( * ) Notice: Subject to any disclaimer, the term of this patent is extended or adjusted under 35 U.S.C. 154(b) by 0 days.

This patent is subject to a terminal disclaimer.

(21) Appl. No.: 15/671,869

(22) Filed: Aug. 8, 2017

(65) Prior Publication Data

US 2017/0336323 A1 Nov. 23, 2017

Related U.S. Application Data

(63) Continuation of application No. 15/198,133, filed on Jun. 30, 2016, now Pat. No. 9,733,181, which is a
(Continued)

(30) Foreign Application Priority Data

Feb. 25, 2013 (GB) .................................. 1303324.6

(51) Int. Cl.
*G01N 21/3581* (2014.01)
*G01N 17/00* (2006.01)
(Continued)

(52) U.S. Cl.
CPC ....... *G01N 21/3581* (2013.01); *G01N 17/006* (2013.01); *G01N 17/04* (2013.01);
(Continued)

(58) Field of Classification Search
CPC ........... G01N 21/3581; G01N 21/3563; G01N 22/02; G01N 21/952; G01N 21/55;
(Continued)

(56) References Cited

U.S. PATENT DOCUMENTS 4,647,220 A 3/1987 Adams et al.
9,518,918 B2 12/2016 Mann et al.
(Continued)

FOREIGN PATENT DOCUMENTS

DE 10 2010 003 112 9/2011
EP 1 650 555 4/2006

OTHER PUBLICATIONS

International Search Report dated Feb. 14, 2014 from International Application No. PCT/EP2013/069746.
(Continued)

*Primary Examiner* — David Porta
*Assistant Examiner* — Gisselle Gutierrez
(74) *Attorney, Agent, or Firm* — Beyer Law Group LLP

(57) ABSTRACT

Wide-angled incoherent millimeter or sub-millimeter electromagnetic waves from an extended active source are used to probe substrates and their protective coatings or outer layers, such as paint or thermal insulation. The incoherent waves provide dispersion and angular variation with respect to angular incidence to the substrate. Illumination of the substrate permits differentiation between un-corroded and corroded sections of the sample because reflectivity, emissivity and/or transmissivity from the substrate or protective coating various according to its homogeneousness. A detector/camera is arranged to identify and resolve differences in detected power within an observed frequency range of the area under test, with this contrast in power being relative to either adjacent areas or anticipated reference levels. The power differences therefore signify the presence or lack of
(Continued)

corrosion or, indeed, the presence of anomalies within or on the substrate or in or under the protective coating or layer applied to the substrate.

7 Claims, 6 Drawing Sheets

Related U.S. Application Data continuation of application No. 14/770,159, filed as application No. PCT/EP2013/069746 on Sep. 23, 2013, now Pat. No. 9,518,918.

(51) Int. Cl.
| | | |
|---|---|---|
| G01N 17/04 | (2006.01) | |
| G01N 21/3563 | (2014.01) | |
| G01N 21/47 | (2006.01) | |
| G01N 21/55 | (2014.01) | |
| G01N 21/952 | (2006.01) | |
| G01N 22/02 | (2006.01) | |
| G01N 22/04 | (2006.01) | |
| G01N 21/88 | (2006.01) | |
| G01N 21/84 | (2006.01) | |

(52) U.S. Cl.
CPC ..... *G01N 21/3563* (2013.01); *G01N 21/4738* (2013.01); *G01N 21/55* (2013.01); *G01N 21/952* (2013.01); *G01N 22/02* (2013.01); *G01N 22/04* (2013.01); *G01N 2021/4764* (2013.01); *G01N 2021/8427* (2013.01); *G01N 2021/8812* (2013.01)

(58) Field of Classification Search
CPC .... G01N 21/4738; G01N 22/04; G01N 17/04; G01N 17/006; G01N 2021/8812; G01N 2021/8427; G01N 2021/4764
USPC .................................................. 250/339.05
See application file for complete search history.

(56) References Cited

U.S. PATENT DOCUMENTS

| | | |
|---|---|---|
| 2001/0042834 A1 | 11/2001 | Kenway |
| 2005/0098728 A1 | 5/2005 | Alfano et al. |
| 2016/0305869 A1 | 10/2016 | Mann et al. |

OTHER PUBLICATIONS

International Preliminary Report on Patentability dated Sep. 3, 2015 from International Application No. PCT/EP2013/069746.

$$T_{eff} = \varepsilon \times T_o + \rho T_e + t \times T_b$$

DETECTION SYSTEM AND METHOD OF DETECTING CORROSION UNDER AN OUTER PROTECTIVE LAYER

CROSS-REFERENCE TO RELATED APPLICATIONS

This application is a Continuation of U.S. patent application Ser. No. 15/198,133, filed on Jun. 30, 2016, which is a Continuation of U.S. application Ser. No. 14/770,159, filed on Aug. 25, 2015 (now U.S. Pat. No. 9,518,918). U.S. application Ser. No. 14/770,159 is a 371 of International Application No. PCT/EP2013/069746, filed Sep. 23, 2013, which claims priority to GB Application No. 1303324.6, filed on Feb. 25, 2013, all of which are incorporated herein by reference in their entirety.

FIELD OF THE INVENTION

This invention relates, in general, to detection systems and is particularly, but not exclusively, applicable to detectors (and detection system methodologies) that operate to assess levels of corrosion under outer protective layers or coatings, such as paint, insulation, fireproof cladding or anti-corrosion protective coatings, applied on or over a surface, such as a pipe or wall.

SUMMARY OF THE PRIOR ART

The detection and identification of structural anomalies and imperfections (including cracks and fractures, penetrations, porosity variations, corrosion, disbanding and delamination) in substrates is important for quality control, preventative maintenance and especially safety considerations. In this context, the substrate can define the structure of a pipe, panel or frame and may be made from a number of known materials, including metal or composite materials. Once in situ, the mechanical structures formed from such substrates are subjected to a variety of environments and/or differing pressures applied internally within or externally to the substrate. For example, general load-bearing can produce bending moments that induce stresses within the substrate. Furthermore, these environments can be chemically corrosive or mechanically abrasive.

In terms of negative outcomes, if we consider a pipe in a chemical factory or an oil pipeline running across a desert, rupturing of such a pipe would shut the entire system down and has environmental and safety impact. More specifically, escaping liquid, such as oil, must be cleaned up and disposed of in a safe fashion, whilst rapid high pressure release of a pressurised liquid travelling in a pipe could result in fragmentation of pipe and, consequently, the generation of high-velocity projectiles from the splintered pipe substrate. Regular maintenance, or predictive maintenance, is therefore essential.

Many aircraft airframes now use composite materials on critical components such as wings and ailerons. These materials are extremely strong provided their structural integrity remains intact, but any crack or delamination can lead to rapid loss of stiffness and may result in catastrophic failure. Regular airframe inspection for air worthiness assessment is therefore critical across significant areas of a plane, with the substrate providing strength to the airframe generally covered by paint that obscures direct inspection.

Once deployed in the field, the cost of assessment and the length of time required for performing the assessment increase simply because of the physical inaccessibility of the part under investigation. In other words, visual or mechanical inspection is difficult simply because of restricted access.

Furthermore, the substrate under investigation is frequently covered by a protective coating or insulating layer applied (typically) at the point of final manufacture or otherwise after assembly in the field. Any covering curtails direct visual assessment, and any covering or coating has hitherto required the use of expensive and accurately located evaluation equipment. Proactive maintenance therefore has a relatively high cost because an assessment of corrosion under insulation ("CUI") or corrosion under paint ("CUP") or corrosion under coatings ("CUC") requires an active peeling back or outright removal of the insulating material or paint to conduct a visual or other quantitative inspection of the substrate, whereafter a new protective coating or layer must be properly and securely reapplied. Removal and reapplication of any coating or layer therefore has a cost, with any removal process providing further potential for damaging the substrate. Situations can, in fact, occur where removal of the protective coating and layer reveals a pipe in an acceptable mechanically-stable condition. In this case, the cost for evaluating the substrate for signs of wear or corrosion could have been avoided since no remedial action would have been necessary.

As an example of a protective coating, Chartek® 7 is a high performance epoxy intumescent fire protection coating system applied to steel, aluminium and other substrates to protect those substrates from the effects of hydrocarbon pool and jet fires. Chartek® 7 is endorsed by many commercial insurers, and is primarily intended for use in high risk environments, such as oil, gas, petrochemical and power generation industries and shipping. FoamGlas® is another form of insulative/protective covering (see http://www.industry.foamglas.com/_/frontend/handler/document.php?id=303&type=42).

GB-A-2398946 (QinetiQ) describes the use of microwave radar detection for surface discontinuities, particularly in the surface of a railway track. A millimeter wave radar system is provided to transmit short pulses of millimeter wave radiation towards the surface under test. If the surface has no flaws or defects, most of the transmitted radiation is reflected in an expected direction. At least one receive antenna is provided to detect whether any transmitted radiation has been scattered from a defect in the surface in a direction other than that of the expected reflection direction. The transmit antenna may also operate as the receive antenna i.e. monostatic, however a bi-static arrangement having separate transmit and receive antennas is preferred. More than one receive antenna may be used to inspect the rail from different angles to provide increased sensitivity and to help in determining the type of defect. The polarisation properties of the scattered radiation may be used in providing information about the type of defect. A further receive antenna may be additionally or alternatively provided in the expected reflection direction to detect a drop in power of the received signal when a defect occurs.

US 2005/0098728—Alfano provides a system and method for non-destructively detecting material abnormalities beneath a coated surface. A terahertz (THz) illumination unit illuminates an area of the coated surface. A detection unit detects light reflected from the illuminated area of the coated surface, and a processing unit images the illuminated area of the coated surface from optical characteristics received from the detection unit. Alfano therefore suggests that most protective paints and coatings are transparent in these wavebands, so corrosion is detectable (in the sense that it can be illuminated and thus observed at particular wavelengths) through paint or many other protective coatings.

Alfano '728 and QinetiQ '946, however, both rely on the sample under investigation to be held at a set distance and orientation from the observing apparatus. More specifically, these prior art systems rely on along axis, line-of-sight or orthogonal illumination from a highly directional source. This illumination approach introduces problems due to specular reflection from the surface, and requires the inspection apparatus (or the sample) to be repositioned at each measurement point. The requirement for detector orientation and/or sample placement imposes severe constraints on the practical implementation of their techniques in real world environments, particularly those found outdoors on bridges, oil platforms and the like where corrosion presents a significant problem. Furthermore, the systems of Alfano '728 and QinetiQ '946 rely on illumination of the sample with directional, coherent millimeter wave, sub-millimeter wave or terahertz frequency sources. The coherent source provides an ability to assess phase in the reflected waves, whereas a non-aligned source is considered problematic from the perspective of feature resolution.

Approaches such as taught in Alfano '728 and QinetiQ '946 rely on careful alignment with the sample and the need to spin, i.e. rotate or reposition, either the inspection system and or the sample under test in order to effectively scan the sample and/or recover (i.e. receive) sufficient data for analysis. Sample or detector rotation both result in significant apparatus complexity and increased cost, with rotation furthermore reducing the speed of assessment. The prior art systems of Alfano '728 and QinetiQ '946 can therefore be considered as laboratory-based executions because their construction makes in situ substrate inspection very difficult, if not impossible, but at least highly impractical. In addition, the use of a powerful artificial coherent source only recovers the reflectivity component of the objects positioned within the scene and so any misalignment or variation of the surface texture of the sample can be misinterpreted as a reflectivity variation even for surfaces free of corrosion, i.e. the systems are subject to a false trigger.

SUMMARY OF THE INVENTION

According to a first aspect of the present invention there is provided a method of detecting the presence of anomalies in or on a substrate covered by a protective coating or layer, the method comprising: observing reflectivity from the substrate arising from incident electromagnetic waves produced from wide-angled illumination from a first incoherent source, the incident electromagnetic waves having millimeter or sub-millimeter wavelengths or having a frequency below about thirty terahertz; identifying the presence of anomalies in the substrate by at least one of: contrasting observed reflectivity in adjacent areas of the substrate; and contrasting observed reflectivity of an area of the substrate under test against a reference reflectivity value anticipated for the area of the substrate under test.

In a preferred embodiment, the first incoherent source is a passive source and the method further comprises: observing reflectivity from the substrate arising from incident electromagnetic waves produced from wide-angled illumination from an incoherent active source that is different to the first incoherent passive source, the incident electromagnetic waves from the incoherent active source having millimeter or sub-millimeter wavelengths or having a frequency below about thirty terahertz; identifying the presence of anomalies in the substrate by contrasting spectral reflectivity profiles observed from the passive source and the active source.

The assessment of structural integrity of a layer on, or coating covering, the substrate may occur by evaluating transmissivity through the layer or coating, the evaluation contrasting differences in the spectral reflectivity profiles observed using the passive source and the active source; and through the step of generating an output in the event that the transmissivity between the observed spectral reflectivity profiles from the passive source and the active source exceeds a threshold.

A preferred method may determine emissivity from the substrate at two different temperatures to assess whether a change in emissivity has occurred between the two different temperatures, with the determination causing generation of an output in the event that the change in emissivity exceeds a predetermined threshold, the output indicating the presence of at an anomaly in or on the substrate.

In a second aspect of the invention there is provided a corrosion detection system for identifying corrosion under a layer or coating, the corrosion detection system comprising: an imaging system including a detector configured to detect, in use, reflectivity from a substrate under test, said reflectivity arising from illumination of the substrate by an incoherent, wide-angled source of electromagnetic waves having a frequency in the range of between about thirty gigahertz and about thirty terahertz; and a processor-based evaluation system responsive to the imaging system, the processor based evaluation system configured to present an indication of a difference in detected reflectivity between at least one of: reflectivity evaluated from a plurality of different areas of the substrate, whereby differences in reflectivity indicate corrosion; and observed reflectivity of an area of the substrate under test against a reference reflectivity value anticipated for the area of the substrate under test, whereby the difference in observed reflectivity relative to the reference reflectivity indicates corrosion.

Preferably, the imaging system is configured to observe reflectivity within at least one of the frequency bands that are transparent to atmospheric water and atmospheric oxygen:

In a further aspect of the invention there is provided a detection system identifying structural anomalies in a substrate covered by a layer or coating, the detection system comprising: an imaging system including a detector configured to receive and detect, in use, reflectivity from a substrate under test, said reflectivity arising from illumination of the substrate by an incoherent, wide-angled source of electromagnetic waves, the configured to observe reflectivity within frequency bands that are transparent with respect to atmospheric water and atmospheric oxygen; and a processor-based evaluation system responsive to the imaging system, the processor based evaluation system configured to present an indication of a difference in detected reflectivity between at least one of: reflectivity evaluated from a plurality of different areas of the substrate, whereby the difference in reflectivity indicates an anomaly; and observed reflectivity of an area of the substrate under test against a reference reflectivity value anticipated for the area of the substrate under test, whereby the difference in observed reflectivity relative to the reference reflectivity indicates an anomaly.

An active incoherent noise source may provide, in use, selective wide-angled illumination of the substrate under investigation, the active incoherent noise source generating at least one of (i) millimeter wavelengths, (ii) sub-millimeter wavelengths and (iii) micron wavelength having a frequency below about thirty terahertz.

In a particular embodiment the processor-based evaluation system is configured to: contrast relative levels of reflectivity from the substrate as produced by said active incoherent noise source and said passive source; and generate an indication of the presence of an anomaly in the substrate in the event that the contrast of measureable parameters for evaluated reflectivity under the active and passive sources yields a difference that exceeds a predetermined threshold.

The processor-based evaluation system may be further configured to provide an indication of confidence in structural integrity of a layer on, or coating covering, the substrate under test, the indication based on evaluating transmissivity through the layer or coating, the evaluation contrasting differences in the spectral reflectivity profiles observed using the passive source and the active source.

In yet another aspect of the invention there is provided a detection system identifying structural anomalies in a substrate covered by a layer or coating, the detection system comprising: an imaging system including a detector configured to receive and detect, in use, electromagnetic frequencies emanating from a substrate under test, said detector configured to observe electromagnetic frequencies within a range between about 30 GHz and 30 THz; and a processor-based evaluation system responsive to the imaging system, the processor-based evaluation system configured to identify a difference in assessed emissivity from the substrate under test based on observing and evaluating emissivity of the substrate under test at at least two test temperatures that each differ relative to a background temperature; wherein the processor generates an output in the event that the difference in emissivity exceeds a predetermined threshold, the output indicating the presence of at an anomaly in or on the substrate.

Advantageously, the embodiments of the present invention provide a detection system and technique that makes use of naturally occurring electromagnetic radiative illumination in the band from about thirty gigahertz (30 GHz) to about 30 THz to reliably detect deformations, penetrations, porosity, fractures, cracks, corrosion, disbands and delamination of a substrate under protective coating and/or layer of insulation. Moreover, the system of the present invention does not require a high degree of accuracy in detector or sample alignment, with this providing a two-fold benefit: i) CUI or CUP or CUC of a sample can be rapidly assessed; and ii) a large area can be investigated and assessed in a relatively short period of time. Since the detector system does not require high precision placement, the cost of the detector system is also modest.

Incoherent millimeter wave, sub-millimeter wave and terahertz test signals are used to probe metal substrates that are covered by a protective coating or outer layer, such as paint or thermal insulation, obscuring direct assessment of the substrate. The incoherent test signals, which may be from a naturally occurring passive source (such as the sky) and/or from an active noise source, provide signal dispersion and angular variation of the test signals with respect to angular incidence to the substrate. Illumination of the substrate permits differentiation between un-corroded and corroded sections of the sample because reflectivity (and emissivity) from a metal-based substrate is heavily dependent on the surface resistivity which in turn is dependent on the corroded state. A detector/camera is arranged to pick up reflections from the substrate and an associated control system identifies regions of the sample that reflect the test signal illumination differently or otherwise indicate a variation from a reference value. The differences therefore signify the presence or lack of corrosion or, indeed, the presence of other abnormalities within or on the substrate.

Naturally occurring passive, incoherent and dispersed millimeter wave, sub-millimeter wave and terahertz illumination of the substrate under investigation permits differentiation between un-corroded and corroded sections of the sample. The detection system supports non-destructive testing and, in fact, in situ (non-disassembly) testing.

The various embodiments provide a system that has the ability to observe the sample directly from a distance without having to be rigidly attached to a reference frame; this freedom offers considerable benefit from the practical implementation in a real world scenario. The use of a passive extended source that provides a wide angle illumination represents a significant improvement over the prior art, particularly for viewing non-flat surfaces such as pipes or upright tubes.

BRIEF DESCRIPTION OF THE DRAWINGS

Exemplary embodiments of the present invention will now be described with reference to the accompanying drawings, in which.

DETAILED DESCRIPTION OF A PREFERRED EMBODIMENT

Figure 1:
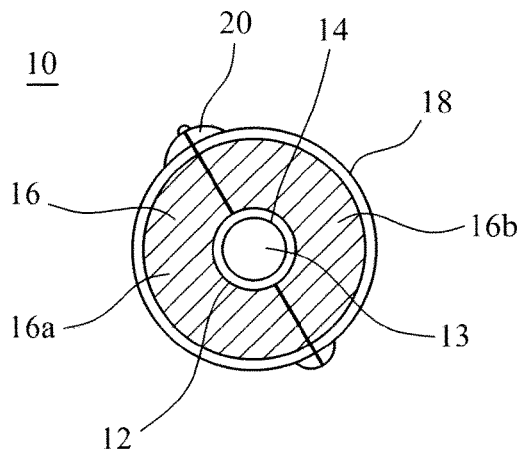
FIG. 1 shows a typical pipework, including a layer of insulation.

FIG. 1 shows a typical pipework system 10. A pipe 12 is made of a substrate that is subject to some form of corrosion 14, such as rusting in the case of an iron-based pipe. The pipe 12 may carry, within its interior 13, any number of materials (including oil or other chemicals) and may be internally lined or its substrate externally coated with a protective coating, such as a paint, or otherwise protected by an external insulating layer 16. In the latter respect, the layer 16 may be a thermal lagging which is secured in placed around the pipe of an external jacket 18. The insulating layer 16 may, in fact, be realised by two hemispheres (16a, 16b) which are clamped together by the external jacket 18 in combination with some form of locking mechanism 20 that acts through the external jacket 18. The skilled artisan will understood the arrangement of the pipework system 10 and how the insulating layer 16 is held in place about or otherwise applied (in the sense of being adhered to) the pipe 12.

The insulating layer 16, which may be a sprayed solution or may include a sprayed coating offering corrosion resistance, is transparent between millimeter and micron wavelengths. Typical materials for the layer (whether insulating and/or protective) include Kevlar-carbon fibre composites and plastics.

Figure 2:
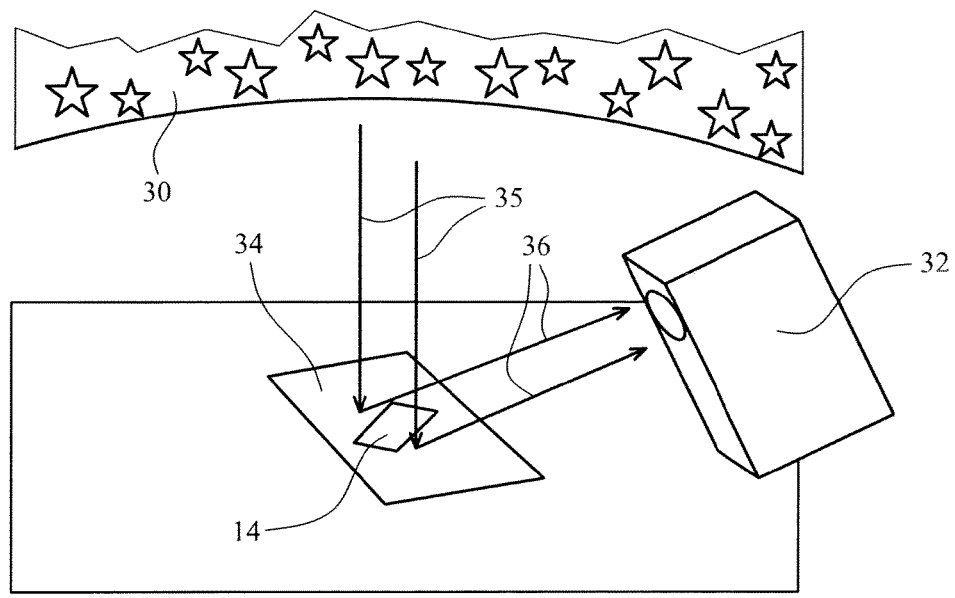
FIG. 2 is a representation of a detection methodology according to a preferred embodiment of the present invention.

FIG. 2 is a representation of a detection methodology according to a preferred embodiment of the present invention. The inventors have recognised that background electromagnetic radiation in frequency select bands from the sky (such as in the millimeter, sub-millimeter and particularly wavelengths in the terahertz range) provide a wide-angle source that, when falling incident on metal, provides illumination of the surface that, upon detection by a suitably wavelength sensitive detector, permits reflectivity from adjacent surface areas of metal to be contrasted. In fact, most non-metallic materials in the millimeter, sub-millimeter and terahertz regions are not fully opaque, but rather have some level of transparency. A non-metallic material's transparency will vary according to its thickness and its dielectric loss tangent which will in turn depend heavily on its structural integrity, purity and water content. Millimeter, sub-millimeter and micron wavelengths are thus capable of penetrating insulation and, consequently, can illuminate metal beneath the insulation. For example, a wavelength of 1.199 mm (nominally 250 GHz) can provide reasonable illumination (and processed imaging) of a metallic surface under a layer of protective paint, although better resolution is achieved with wavelengths of about 0.300 mm (nominally 1 THz), with these higher frequencies still capable of penetration of surrounding insulation and higher surface reflection. Indeed, in general, reflectivity contrast is worse at lower frequencies. It is noted that penetration is worse for higher frequencies, although the contrast in reflectivity of the substrate is higher at higher frequencies.

This 30 GHz to 30 THz range within the electromagnetic spectrum corresponds to a wavelength range of about ten millimeters to about ten microns. Over this range, detector technology with the sensitivity required to measure the natural occurring electromagnetic radiative illumination is commercially available. This range also approximately corresponds to useful thickness of composite, insulating and protective substrates and layers in commercial use in the aero, car, oil, gas, chemical, energy, building (including infrastructure) and shipping industries. The techniques and evaluation systems of the preferred embodiments can therefore, for example, look for damage to aircraft wings and the inspect paint layers for quality and depth. The system can be employed to evaluate hulls of ships (both inside and outside), decking and flooring, such as around toilets. Storage tanks, pressure vessels and tanker piping can be evaluated for structural changes, as can other piping and gantries used on oil platforms, chemical plants and drilling rigs. The invention therefore has wide applicable in evaluation systems to infrastructure in general, including support cables and bridges.

It has now been appreciated that the natural illumination of the sample will occur in an outdoor environment due to the source environment being at a different temperature to the sample environment. The sky 30, for example, is extremely cold due to the cold cosmic background of outer space being visible through the Earth's atmosphere. The environs around the sample are likely to be relatively hot with respect to the sky, with this temperature differential providing good passive illumination conditions.

Since the substrate under investigation can be considered to be generally homogenous, contrasts in reflectivity allow differentiation of, and therefore identification of, areas of corrosion (or malformation) relative to areas having higher substrate integrity. In other words, the inventors have recognized that an active illumination of a substrate with a broadband noise source 35 (such as from the sky/outer-space 30 at wavelengths of up to about 10 microns and a source temperature at seventy-three Kelvin) provides wavelength scattering onto a substrate surface 34, with emissivity/reflectivity 36 from the substrate surface 34 (at nominal room temperature of 293K) detectable by a suitable camera/detector 32. More specifically, by using the naturally occurring, wide-angle illumination in the aforementioned bands of the electromagnetic spectrum, it is possible to image the sample area using a passive 'receive only' camera, such as those now readily available. The nature of the selected source negates the need for the camera/detector 32 to be held at a specific distance or orientation relative to the sample. Furthermore, because the reflectivity of all metals is heavily dependent on the surface resistivity which in turn is dependent on the corroded state, the technique of the preferred embodiment can be used to identify regions of the sample that reflect the illumination differently, thereby signifying the presence or lack of corrosion (or other abnormalities, as mentioned herein) in or on the substrate.

More particularly, the sample illumination principle of the preferred embodiment in the context of an outdoor environment results in the cold signal from the sky being reflected from the surface of the underlying metal, through the paint which is transparent at these wavelengths, and into the passive receive only imaging camera. Corroded areas beneath the paint reflect the cold sky signal less strongly due to the higher surface resistivity associated with corroded metal. Corroded areas in this instance shows up as being warmer than the un-corroded area. The strength of the difference in signals gives an indication as to the level of corrosion. The sky therefore provides a cold noise source.

In terms of the camera/detector 32, one might use a typical capture rate of ten frames per second or lower, subject to the number of detectors (whether based on a raster arrangement or rotating optics) available within the camera system. The camera optics may therefore include scanning and focusing mirrors; these configuration will be discussed below. Camera positioning is typically about thirty centimeters above the source, although position will depend on the signal strength, optical resolution and size of expected defect. Typically, sample area assessment will cover about 100 $cm^2$ to 1000 $cm^2$ and will occur over a range of about one second to five seconds. Camera operation is a design choice and relates to speed and resolution, as will be understood.

The camera may be linked to a display that provides an image or representation of the substrate's physical integrity, homogeneity and/or state of corrosion. The camera, and particularly its control processor, may be configured to provide a numeric report of the sample cross-referenced to the location of the sample relative to a known reference point.

Figure 3:
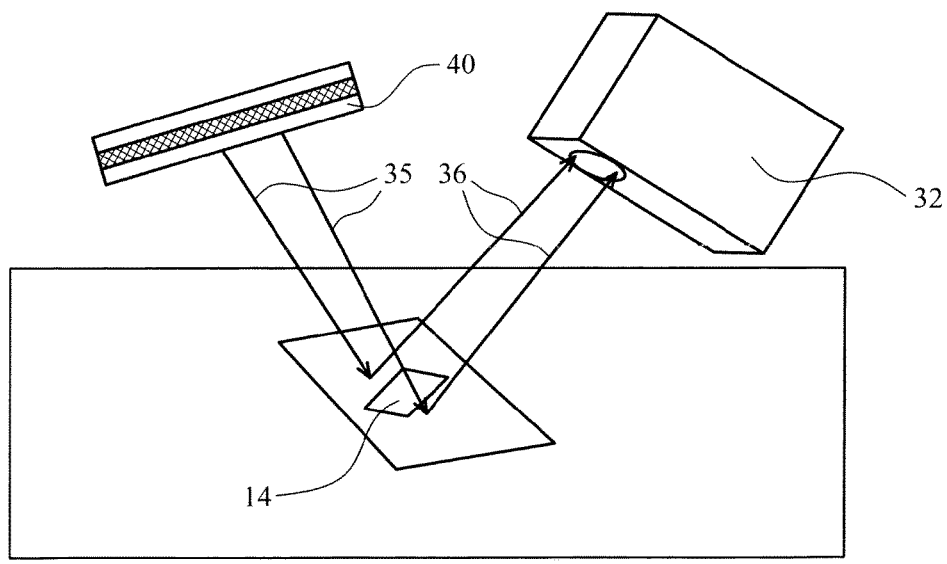
FIG. 3 is a representation of a detection methodology according to an alternate embodiment of the present invention.

In FIG. 2, the sky provides a wide-angled illumination from a passive source of millimeter and sub-millimeter wavelengths and terahertz frequencies. In contrast, FIG. 3 is a representation of a detection methodology according to an alternate embodiment of the present invention, with the source of incoherent wide-angled millimeter and sub-millimeter wavelengths and terahertz frequencies provided from a local, extended source 40 nominally operating at about 473K (e.g. the extended source 40 is an infra-red source that is also highly emissive in the millimeter and sub-millimeter wavelengths and terahertz frequencies; such sources are readily known). The arrangement of FIG. 3 therefore compensates for natural environmental conditions that are not ideal for assessment, e.g. when dense cloud may weaken the signal from the cold sky or when the sample being investigated is indoors. For these conditions, active illumination can be achieved using an extended black body that either replaces or augments the passive signal originating from the sky. With respect to the nature of the black body extended source, this can be selected to be either hotter or colder that ambient conditions, but a substantially temperature difference relative to ambient should exist in the vicinity to the sample. For example, a black body having a temperature in the range of about 450 k to about 550K provides a temperature differential relative to ambient of between about 130 k to about 250 k. The black body extended source thus represents a broadband noise source arranged to provide scattering. The configuration of an extended black body in accordance with the embodiments of the present invention is readily known to the skilled addressee.

For detection of a reflectivity from the sky as the cold passive source, it is noted that a reflector may be used to image the sky onto the test surface. The reflector is therefore has an adjustable inclination. Furthermore, in terms of detector operation for a passive cold sky, the detector 32 takes into account that the atmosphere must be transparent and, consequently, the detector operates in frequency bands (i.e. atmospheric windows) that are transparent with regard to atmospheric water and atmospheric oxygen. A preferred embodiment for the detector using the sky therefore looks to reflectivity responses especially in optimized frequency bands (i) between about 30 GHz and about 60 GHz, (ii) between about 65 GHz and about 100 GHz, (iii) between about 120 GHz and about 157 GHz, (iv) between about 160 GHz and about 181 GHz, (v) between about 185 GHz and about 270 GHz and (vi) between about 320 GHz and about 360 GHz. Reflectivity evaluation from the sky as a cold source does not occur above 500 GHz. Operating at different frequencies using the sky as a passive cold source can occur with increasing altitude since the attenuating effect of atmospheric water and atmospheric oxygen is reduced.

Figure 4:
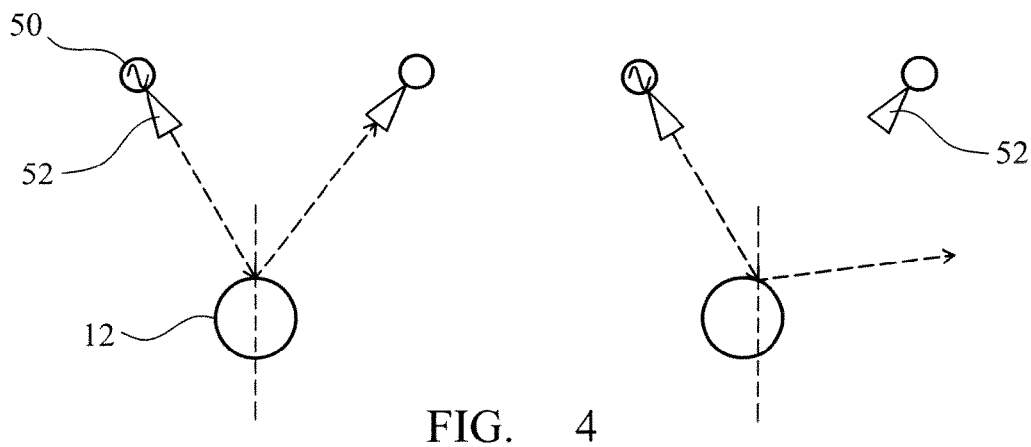
FIG. 4 illustrates the detection limitations of a coherent source relative to a spherical or cylindrical test substrate.

In FIG. 4 a round test sample (such as a cylindrical pipe 12) is illuminated with a coherent directional millimeter, sub-millimeter wavelengths or terahertz frequency source 50. Directionality is provided by a suitable horn or waveguide 52. Provided that the detector's spatial positioning corresponds to the angle(s) of reflection from the surface, the detector will receive some signal for processing and evaluation typically controlled by a local processor configured to execute program code that renders an image or provides a numeric representation (or other indication) of adjacent test areas within the pipe' substrate. However, with cylindrical pipes, the angle of reflection of an incident electromagnetic wave is severely altered by the striking position of that electromagnetic wave on the pipe; this means that a statically-positioned receiver 52 having a limited receiving angle will not receive adversely angled reflections (and the flux density of reflected electromagnetic waves therefore relatively low). Expressing this differently, when the source and detector are positioned symmetrically on the central axis of a cylinder, a coherent narrow source achieves a significant reflected flux density of reflected waves into the receiver, but once the source and detector lie off the central axis then the signal emitted by the directional is reflected by the cylinder to miss the detector.

The prior art solutions in Alfano '728 and QinetiQ '946 work on the premise of FIG. 4 since they make use of highly-controlled, position-orientated systems because they make use of a local directionally-targeted source and a receiver positioned to receive any reflection. Specifically, as will be now understood, Alfano '728 and QinetiQ '946 rely on "along axis", line-of-sight or orthogonal illumination from a highly directional source, with this introducing problems from specular reflection from the surface and requiring the apparatus or the sample to be repositioned at each measurement point. Quite simply, the prior art evaluation systems fail to make use of natural millimeter waves, sub-millimeter waves or terahertz frequency signals either reflected or emitted by the substrate itself or those signals emitted from the substrate's surroundings and subsequently reflected from the substrates surface.

In contrast, the preferred embodiments of the present invention make use of either a naturally occurring wide-angled source and/or an extended local source, but in both cases these sources are incoherent and nominally omnidirectional (in that emissions from the sources angularly dispersed). As will be understood with reference to FIG. 5, an incoherent, extended omni-directional terahertz source compensates for surface irregularities by ensuring that the flux density 54 of reflected electromagnetic waves is sufficiently high at the camera/detector 32 irrespective of the relative strike angle of electromagnetic waves from the millimeter, sub-millimeter wavelengths or terahertz frequency source to the cylindrical surface of the pipe 12.

The preferred embodiments of the present invention therefore make use of an appreciation of the penetrating but reflective and emissive capabilities of a select band of wavelengths in association with the benefit of wide-angled illumination from an incoherent source.

More particularly, although reflectivity and emissivity signals from naturally occurring sources are extremely weak, it has been recognized by the inventors that they provide a source of valuable information concerning substrate homogeneity or substrate integrity. Specifically, a passive source (such as the sky) permits assessment of the emissivity or reflectivity of the substrates surface, or the substrate's transmissivity of its interior in the case of a composite or use of any protective or insulating layer. Indeed, continuous metal substrates and materials are fully opaque, although their surface reflectivity in the millimeter, sub-millimeter and terahertz regions will depend highly on its surface resistivity and/or any coating or corrosion layer.

In fact, embodiments of the present invention may make use of both a passive wide-angled source and an active wide-angled millimeter, sub-millimeter wavelengths or terahertz frequency source. Using a passive source, reflectivity from a substrate's surface can be determined and contrasted against a known reference reflectivity value for nominally the same homogeneous substrate in acceptable (and preferably perfect) condition. Any variation in reflectivity between the measured value and the reference value therefore provides an indication of substrate degradation, e.g. rusting or pitting and other structural defects (as outlined herein). Rusting or other structural anomalies will therefore see a relative decrease is reflectivity. The reference value can be determined from empirical testing of a new, pristine substrate at the point of installation/manufacture or otherwise from accepted international standards.

In the event that the passive, wide-angled incoherent source is substituted for an active wide-angled incoherent noise source, detectable reflectivity in the millimeter, sub-millimeter and terahertz frequencies spectrum swamps other local measureable effects (such as emissivity) associated with the test substrate. Consequently, save for magnitude in the detected signal, the same area of the substrate should have an identical (or near identical) reflectivity profile under both active and passive illumination. In the event that there is a noticeable variation—which can be determined by comparison of data points using a computer program or by visual inspection of a plot on a display or printout—between profiles for the area of substrate, then the variation infers a change in transmissivity of the surrounding insulation (whether a protective paint or thermal protective barrier) and therefore identifies a fault requiring remedial action or additional monitoring. Furthermore, the system may be configured to evaluate a change in transmissivity based on expected or reference values for the protective layer or coating that supposedly protects or shields the surface area of the substrate that is under reflectivity evaluation. In other words, a leak of water or other fluid into the surrounding protective layer or coating that covers the substrate brings about a detectable change in transmissivity characteristics in the protective layer or coating as reflected by changing spectral profiles in the millimeter, sub-millimeter and terahertz frequencies spectrum under active and passive illumination conditions. In other words, the contrast between active and passive reflectivity profiles infers a change in transmissivity when the two reflectivity profiles differ for the same area under active and passive incoherent wide-angled illumination. The system's software may appreciate a meaningful difference based on exceeding of a threshold value summed across the selected common spectrum used for reflectivity in both the active and passive test phases, or it may be based on an absolute number.

The trigger and method that are selected from assessing a meaningful change that potentially infers corruption or contamination of the layer or coating will be readily appreciated by the skilled artisan.

The detection and evaluation system of the present invention is therefore configured to identify the change or suspected change in homogeneity (such as determined by contrasting of spectal profiles for reflectivity measurements observed under passive and active incoherent, wide-angled terahertz illumination environments) by generating a sensory warning or output. Typically, the detection and evaluation system is realized in software (executed by a control processor) and is therefore responsive to spectral data captured and imaged by the camera/detector 32 of, for example, FIG. 5. The camera/detector are part of a processor controlled imaging system that is configured to evaluate spectral responses across the 30 GHz to 30 THz band, although specific and relatively narrow frequencies windows may be selected within this relatively broad band (such as described under passive cold illumination by the sky).

In summary, by measuring a non-metallic coating's apparent transmission properties ("transmissivity"), any material variation, structural defect or impurity ingress in the coating (or applied layer, as the case may be) will produce a signal contrast that can be resolved and flagged for attention. For example, the contrast may be viewed as a spike on a display, which spike arises because the output from the camera/detector 32 produces a higher voltage at a first point of substrate inspection relative to a second point of substrate inspection.

With respect to passive detection, it has furthermore been appreciated that reflectivity is not the only contributing component in the detected signal profile within the millimeter, sub-millimeter and micron spectrum; emissivity is also a factor. An evaluation of emissivity from a surface in the millimeter, sub-millimeter and micron spectrum is also contemplated in operating methodologies of the present invention, which evaluation process is particularly applicable to the corrosion assessment in substrates covered by a layer or coating. The camera/detector 32, however, observes a total power signal in the millimeter, sub-millimeter and micron waveband because passive reflectivity and emissivity cannot be resolved directly from a single assessment of an area of a substrate.

For a substrate that is covered by a coating or protective layer, emissivity evaluation will always require a temperature differential between the test substrate's surface and its surroundings.

The reflectivity and emissivity components in the observed 30 GHz to 30 THz spectrum can be differentiated by introducing a thermal difference for the substrate between two separate measurements. So, for the example of a pipe behind insulation, the pipe could be first imaged with cool liquid running through it and then imaged with hot liquid running through it. The metal pipe would reach thermal equilibrium quickly due to the conduction of heat through metal, whereas the surrounding insulation would reach thermal equilibrium much more slowly due to the convection processes. The level of contrast enhancement seen shortly after the thermal differential is established would therefore give an indication that it is the surface of the substrate that has corrosion as opposed to the insulation having a contaminant with decreased transmissivity.

A minimum temperature differential may be in the region of about one degree Centigrade, although thermal differences may be tens and preferably many tens if not hundreds of degrees. More specifically, the camera/detection 32 and particularly the related control software is configured to contrast substrate areas over time to allow for relative temperature variations between the substrate under test and its surroundings to be assessed. Particularly, it is noted that higher emissivity is observed in the presence of surface defects, such as rusting. The emissive source, in this respect, may be the substrate itself given that the substrate may represent a physical barrier (such as a pipe) between an outside coating at a first temperature on an outside of the substrate and a fluid at a different and in contact with an inner surface of the substrate.

From the perspective of assessing emissivity, an external source that has an opposite temperature signature will enhance contrast. For example, a hot pipe in a cold natural passive background will have a higher contrast than a cold pipe in a cold background. This is because the emissive defect will emit more hot signal and reflect less cold signal than the higher reflectivity of any un-corroded region. The same would be true for a cold pipe in a hot background. For materials at elevated temperature the relative emissivity of the material can therefore be used to provide a spectral contrast that is indicative of the presence of a local impurity or else a structural change in the substrate.

This undesirable specular reflection issue experienced with prior art systems is addressed because the thermal source of the preferred embodiments is extended in area and generally (if not completely) omni-directional or random in terms of the origin and direction from which the signal (from, e.g. the sub-millimeter source) is emitted towards the sample under investigation. Consequently, the curvature of the sample does not prevent reflected waves from entering the camera aperture, irrespective of the camera/detectors position above the sample. Indeed, the wide angled source means that a significant proportion of the cylinder can be viewed simultaneously by the camera; this dramatically increases speed of assessment whilst reducing cost and improving the suitability for in situ measurements in a typical industrial environment.

The random scattering from the extended incoherent source 40 mitigates specular reflection through averaging. Indeed, the inventors have appreciated that wide angled illumination therefore eliminates false triggering by increasing flux density in reflections falling incident on the detector array in the receiver.

Figure 6:
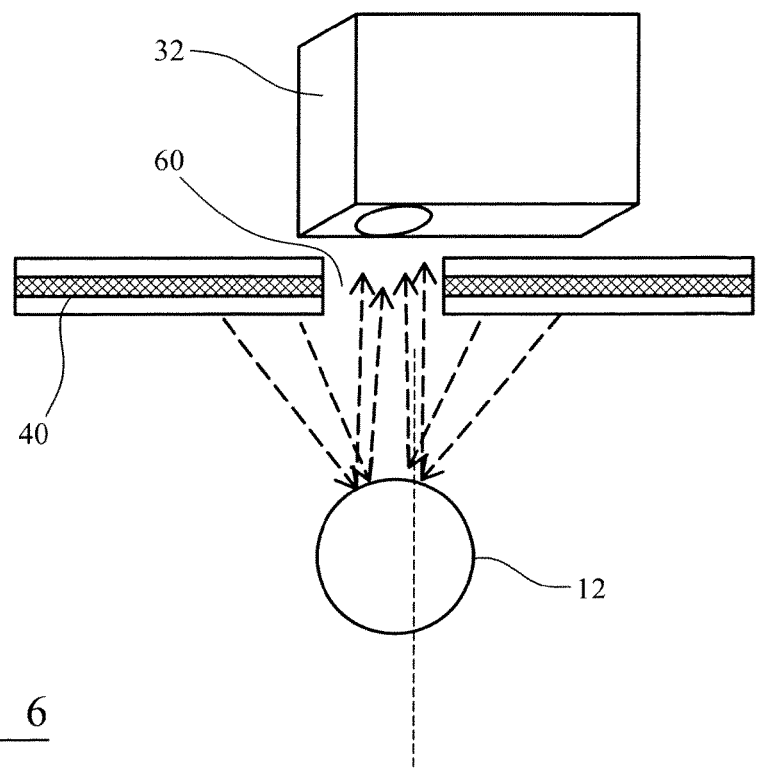
FIG. 6 is a schematic representation of a preferred detection system for identifying corrosion under insulation.

FIG. 6 is a schematic representation of another preferred detection system for identifying corrosion under insulation (CUI), with the configuration particularly appropriate in limited space environment where access to the sample is restricted. In FIG. 6, it is noted that the camera/detector 32 (including associated control electronics) is located behind an aperture 60 in an incoherent extended source 40 that provides a wide angle illumination from randomly scattered electromagnetic waves at millimeter and sub-millimeter wavelengths or low terahertz frequencies. In FIG. 6, the camera/detector looks through a hole in the extended source allowing both to be positioned along the camera's boresight.

Figure 5:
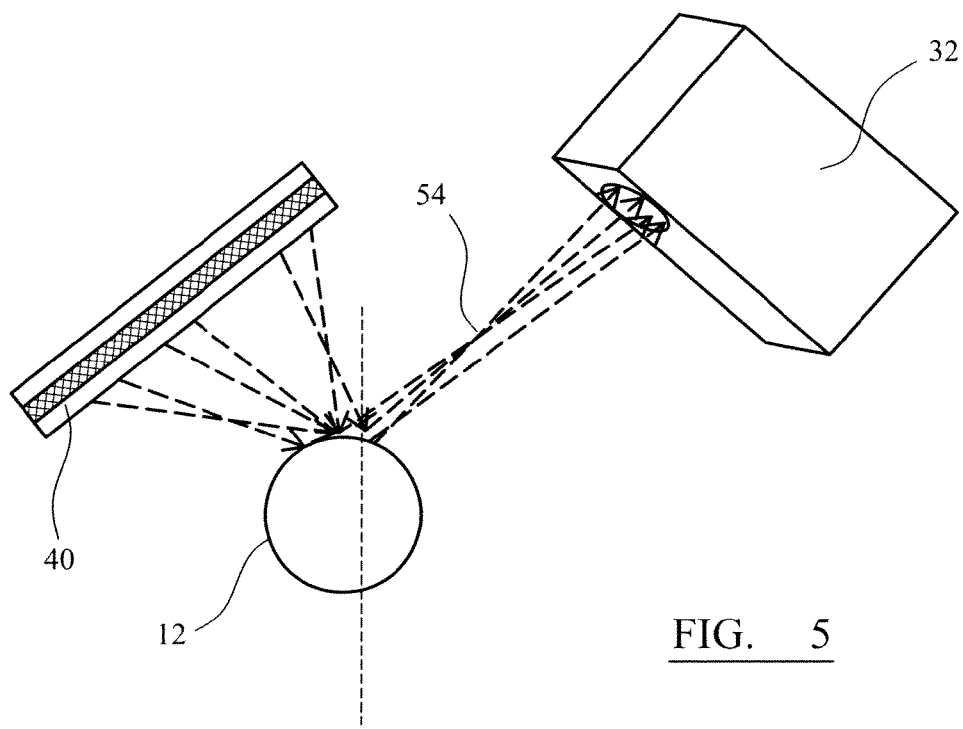
FIG. 5 is a representation of a preferred detection methodology showing the effects of using an incoherent, extended omni-directional terahertz source.

Furthermore, for some applications, the extended source of FIGS. 3, 5 and 6 may have a surface that is curved around a radius, thereby increasing the sample area that can be viewed simultaneously.

The nature of the source as employed in the various embodiments of the present invention provides a significant advantage over the prior art, especially when viewing non-flat surfaces such as pipes or upright tubes.

Passive and active illumination is therefore supported by the preferred system of the present invention, with a change in operating mode selectable by energization (or not) of the local active, incoherent wide-angled source.

Figure 7:
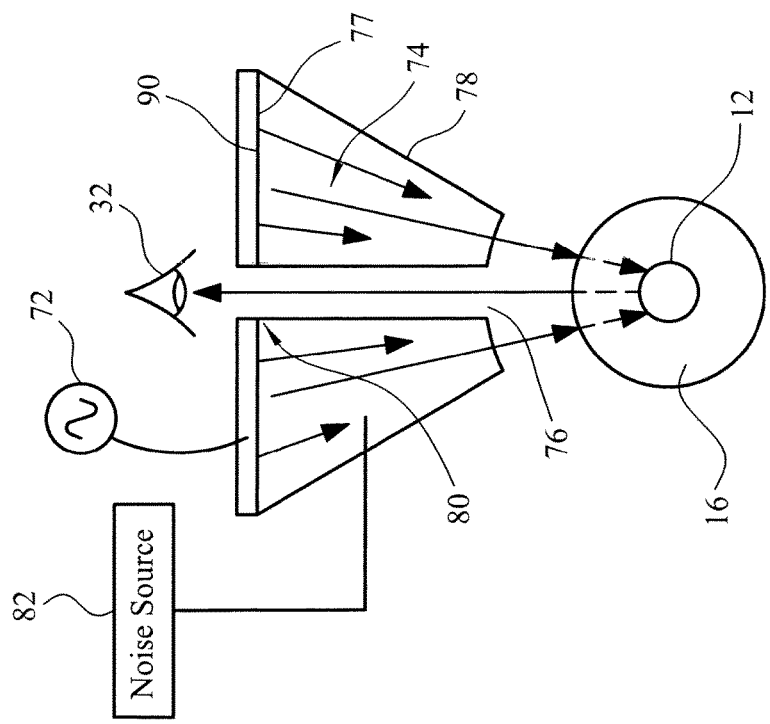
FIG. 7 shows an embodiment for an active source of the CUI or CUP or CUC detection system of FIG. 6.

FIG. 7 shows an embodiment for an active source of the CUI detection system of FIG. 6. In FIG. 6, the camera/detector 32 is located behind an aperture formed in an extended heater element 70 coupled to a power supply 72. The heater is located at the rear of a housing 74 that has an aperture 76 through which emissions from the heater's surface 77 can propagate. At least one feed horn, and typically multiple feed horns 78, 80, are held in an array that physically spaces the feed horn(s) from the heater's surface. Each feed horn 78, 80 is coupled to a noise source 82 that provides signals having millimeter or sub-millimeter wavelengths or low terahertz frequencies. Electromagnetic radiation emanating from the feedhorns 78, 80 is therefore directed on the heater's surface 77 and randomly reflected from that surface in the direction of the aperture 76 and therefore towards the sample, such as a pipe 12, under investigation. The heater 70 therefore provides energy to the random and active noise environment created from the feedhorns 78, 80 within the housing 74. As an alternative configuration, the noise source could be located behind the heater element 70 such that test signals in the millimeter, sub-millimeter or micron wavelengths are fired through the heater element.

Figure 8:
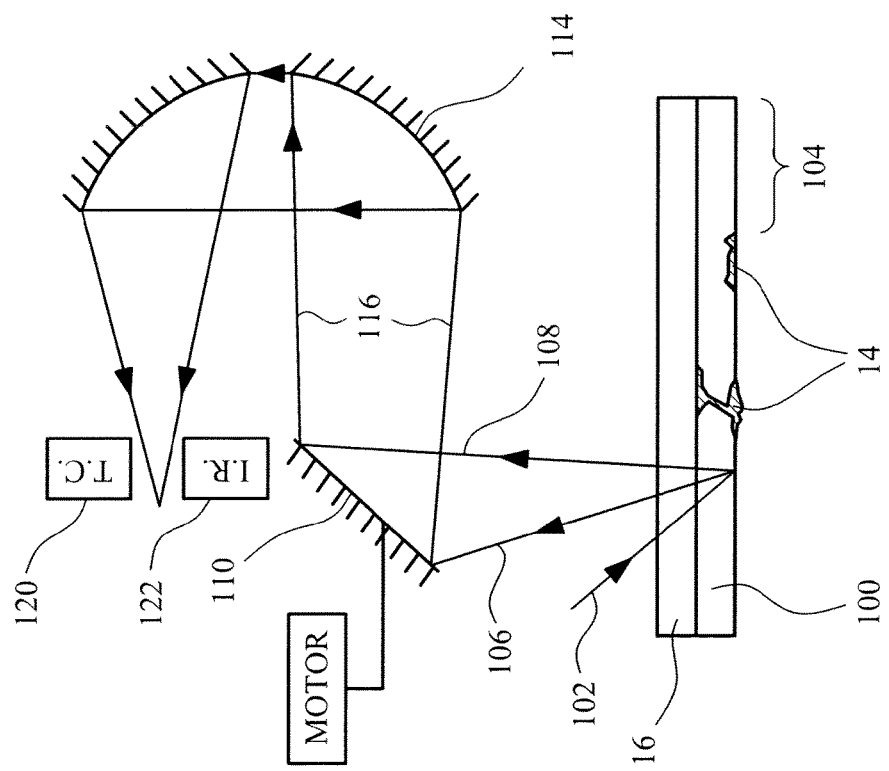
FIG. 8 is a representation of an optical transmission path in a preferred receiver of a corrosion evaluation system.

FIG. 8 is a representation of an optical transmission path in a preferred receiver of a corrosion evaluation system. FIG. 8 shows a sample under investigation, which sample includes a substrate 100 and an insulating or protective layer 16, such as lagging or paint. The substrate 100 includes areas 104 of pristine metal or metal composite, and spots of corrosion or structural defects 14. An incoming electromagnetic wave 102 in the millimeter or sub-millimeter wavelengths (or a terahertz frequency below about 30 THz) is reflected from the substrate, with these reflections 106, 108 reflected from a mirror and preferably a motor-controlled scanning mirror 110. The optional motor and associated drive 112, coupled to any scanning mirror 110, provides tilt and pitch control. Complementary collimating mirrors 114 redirect reflected electromagnetic waves 116 from the scanning mirror (or its stationary equivalent) and act to focus the reflected electromagnetic waves 116 towards sensors, such as a thermocouple 120 and an appropriate millimeter or sub-millimeter wavelength (or terahertz frequency) detector 122. The arrangement of FIG. 7 therefore allows multiple characteristic assessments of a sample under investigation to be conducted simultaneously. For example, higher confidence in identifying CUI or CUP can be obtained by using analysis of complementary bands, such as an infra-red spike that identifies a hot spot on a substrate and where the same area having the hot spot shows a variance in resistivity away from an expected value or spectral profile. Alternatively some coatings are also partly transparent in the infrared region of the electromagnetic spectrum and so anomalous features seen in the infrared which could be due to surface structure or variations in thickness and not corrosion could then be directly attributed to corrosion if they are also present in the millimeter, sub-millimeter wavelength and terahertz frequency bands increasing confidence.

From a practical perspective, a radiometer using a heterodyne mixer or low noise amplifier can be the basis for a detection device in the gigahertz spectrum. At higher frequencies, a quantum cascade laser could be used as a noise source, with detection (or imaging) achieved using a quantum well detector and/or a Schottky detector. Detection devices capable of working in the millimeter wavelength to multi-terahertz spectrum are known, such as outlined in the article: "CMOS DETECTORS: Terahertz imaging achieved with low-cost CMOS detectors" in Laser Focus World (http://www.laserfocusworld.com/articles/2011/07/cmos-detectors-terahertz-imaging-achieved-with-low-cost-cmos-detectors.html).

Figure 9:
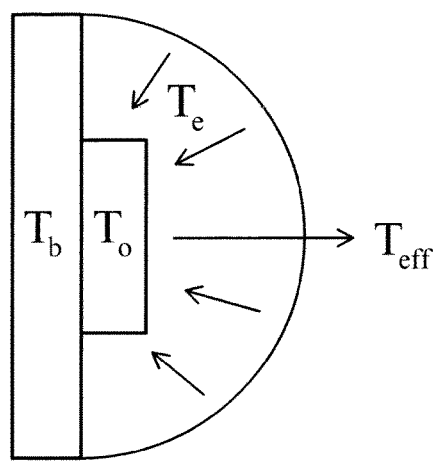
FIG. 9 illustrates the origin of radiometric components that contribute in a signal viewed by the corrosion evaluation system of, for example, FIG. 6.

FIG. 9 illustrates the origin of the radiometric components that contribute in a signal viewed by the corrosion evaluation system of, for example, FIG. 6. When observing an object, such as a substrate of a pipe, a passive millimeter wave, sub-millimeter wave or terahertz frequency radiometer cannot distinguish the actual physical temperature of that object. It can only determine the effective temperature ("Teff") of the object. FIG. 9 shows the relationship between:

i) the measured $T_{eff}$;
ii) the object's physical temperature $T_o$;
iii) the environment's temperature $T_e$;
iv) the temperature of the background behind the objects $T_b$;
v) the objects transmisivity t;
vi) the object's emissivity $\in$; and
vii) the object's reflectivity $\rho$.

The effective temperature $T_{eff}$ is expressed mathematically as:

$$T_{eff} = \in T_o + \rho T_e + t T_b$$

The sensor (with the detector 32) of the various embodiments is arranged to directly measure Teff and, so provided the physical temperature of the environment, the object or the background doesn't vary or is separately monitored, any variation in Teff will indicate either a change in the substrates reflectivity or emissivity or any intermediary layers transmissivity. Any or all of these parameters (singly or preferably in a combination of at least two) can be used to indicate the presence of a defect in the covering layer or surface corrosion of the underlying metal. Indeed, these measureable parameters can be remotely monitored without any careful instrument alignment, whilst any elevation in temperature of the substrate against the environment or background can enhance the contrast due to the presence of an increased signal. Similarly, for composite materials, the internal structure can be investigated by looking through the sample at a target positioned in the background that is held at either an elevated or depressed temperature.

Figure 10:
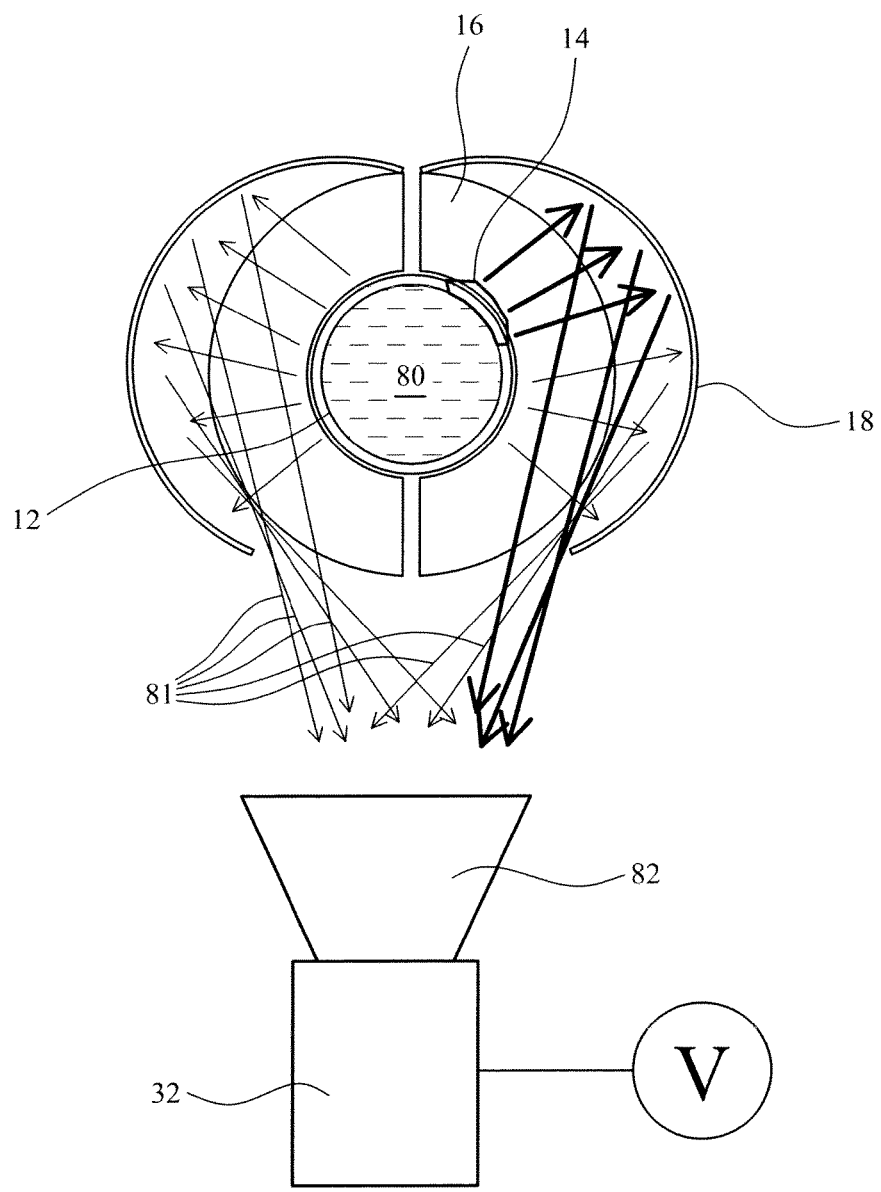
FIGS. 10 and 11 show a corrosion detection system of an embodiment of the invention that makes use of emissivity in evaluating the presence of corrosion under a layer.
Figure 11:
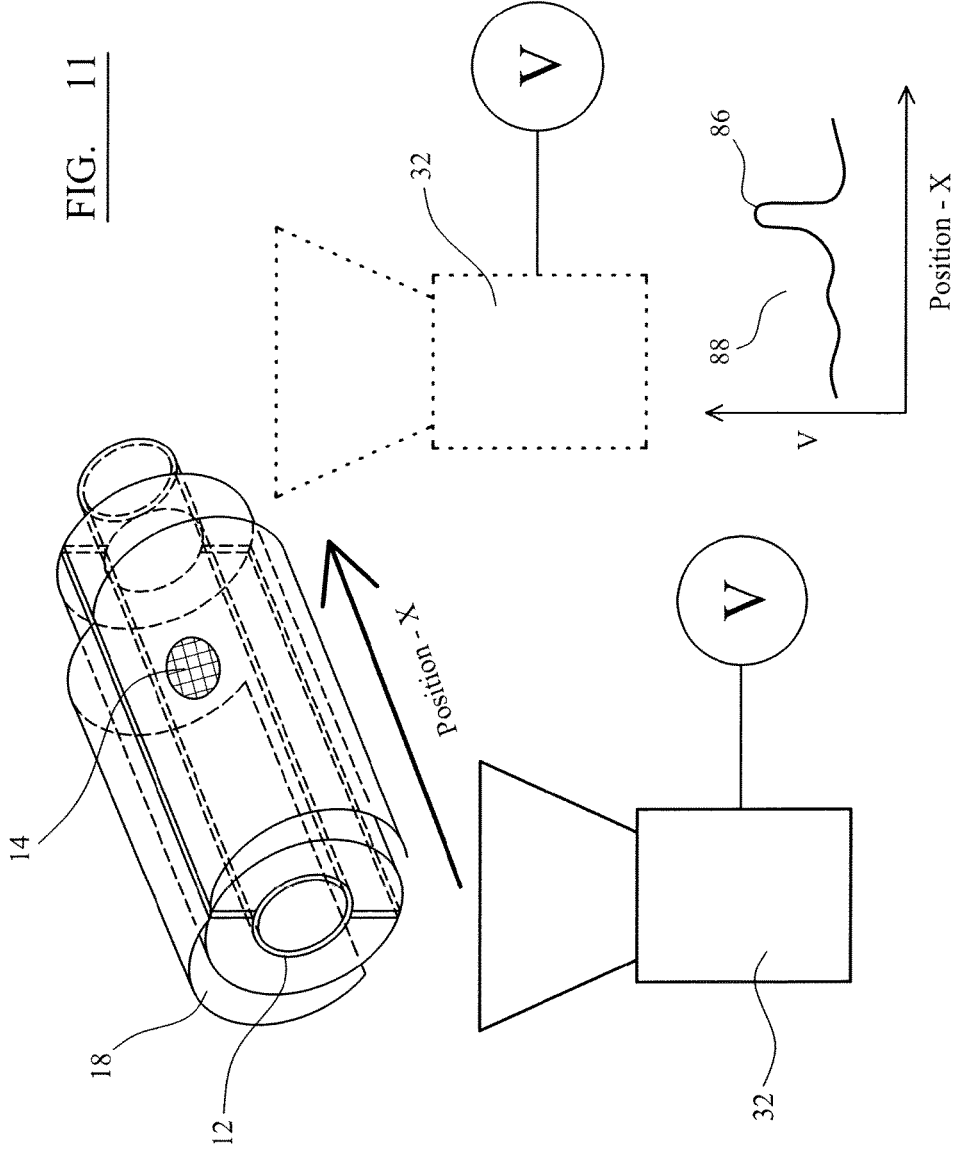

FIGS. 10 and 11 show a corrosion detection system of an embodiment of the invention that makes use of emissivity in evaluating the presence of corrosion under a layer.

In FIG. 9, a pipe 12 acts as a conduit for hot fluid or hot liquid 80. The pipe 12 is encased in insulation 16 and this, in turn, is held in place by a metal jacket 18. The metal jacket is opaque and therefore impervious to direct inspection with millimeter, sub-millimeter of micron test signals (irrespective of whether delivered by a passive or active source). However, the metal jacket can be cracked open to permit the detector to evaluate emissivity from the surface of the pipe under hot and cold transfer conditions. The metal jacket acts to reflect electromagnetic waves 81 (in the millimeter, sub-millimeter of micron range) towards a receiving cone 82 of the receiver/detector. Since emissivity increases—the relative width of the arrows in FIG. 9 reflects relative magnitude—with the presence of corrosion, a voltage spike 86 in an output 88 from the detector (when plotted against position of the detector with respect to the length of the pipe 12) is observed when such structural anomalies, e.g. surface corrosion, are present. The precise circumferential position of any surface anomaly cannot be resolved since reflections from internal surfaces of the metal jacket 18 cannot be individually resolved from the perspective of their individual points of origin. However, by running the detector along the length pipe (as represented in FIG. 10), variations in emissivity are revealed in a suitable parameter plot against position.

Unless specific arrangements are mutually exclusive with one another, the various embodiments described herein can be combined to enhance system functionality and/or to produce complementary functions in the effective assessment and detection of corrosion under insulation ("CUI") or corrosion under paint ("CUP") or corrosion under coating ("CUC"). Such combinations will be readily appreciated by the skilled addressee given the totality of the foregoing description. Likewise, aspects of the preferred embodiments may be implemented in standalone arrangements where more limited functional arrangements are appropriate. Indeed, it will be understood that unless features in the particular preferred embodiments are expressly identified as incompatible with one another or the surrounding context implies that they are mutually exclusive and not readily combinable in a complementary and/or supportive sense, the totality of this disclosure contemplates and envisions that specific features of those complementary embodiments can be selectively combined to provide one or more comprehensive, but slightly different, technical solutions. For example, the use of emissivity to evaluate structural anomalies in pipework carrying fluid (and particularly heated fluid) can be implemented independently of an evaluation system making use of reflectivity to identify structural variance that potentially requires further investigation or repair. Evaluation of the presence (or absence) of corrosion and/or anomalies in or on the substrate or in or under the protective layer or coating can look at contrasting one, two or all of the detected powers associated with (i) reflectivity, (ii) transmissivity and/or (iii) emissivity (with each of those detected powers further evaluated at one or more different temperatures) in the observed frequency range with (a) detected powers arising from naturally-occurring passive illumination of the substrate, protective coating or layer in the in situ environment, or (b) a detected power emanating from the substrate or protective coating or layer as a consequence of its active illumination, or (c) anticipated/predefined reference levels for reflectivity, transmissivity and/or emissivity for the material, construction and/or structure of the substrate, protective coating or layer.

Unless the context otherwise requires a more limited interpretation, the terms CIC, CUC and CUI should be considered to be identical in that each contains a substrate covered by a protective coating or layer. Generally, as will be understood, the shape of any such layer or the form of its application to the substrate is not deterministic with respect to operation of the corrosion or anomaly detection system of the various embodiments of the present invention.

It will, of course, be appreciated that the above description has been given by way of example only and that modifications in detail may be made within the scope of the present invention. In the context of this description, the term "substrate" will be understood to relate to any substrate that reflects millimeter, sub-millimeter of terahertz electromagnetic waves at a level suitable for detection by a camera, with the term "substrate" taking into consideration both generally flat or curved surfaces. The terms "corrosion", "anomalies" and "abnormality" shall be understood to be interchangeable and include manufacturing defects or changes in structure that have been brought about by erosion or corrosion, with each of these terms viewed broadly unless the specific context requires a more limited interpretation. Structural anomalies may therefore relate to imperfections (including cracks and fractures, penetrations, porosity variations, corrosion, disbanding and delamination) in or on substrates located between paint and/or other forms of insulation or covering.

The imaging system of the various embodiments is generally processor based in that data is processed for presentation to the operator by audible or visual display. It will be understood that the imaging system could, however, just provide an optical output (without data processing), which arrangement would then require operator interpretation albeit that the imaging system is responsive to operation of a microcontroller or the like.

The present invention therefore supports in-field testing of pipe networks for preventive maintenance, but equally the detection system can be employed as a final quality control process at a manufacturing facility.

The invention claimed is:

1. A method of detecting the presence of anomalies in or on a substrate covered by a protective coating or layer or detecting the presence of anomalies in or on the protective coating or layer applied to the substrate, the substrate in an in-situ environment, the method comprising:
   observing, in an observed frequency range, at least one of reflectivity, transmissivity and/or emissivity from an area of interest under investigation on or in the substrate or on or in or under the protective coating or layer, said reflectivity, transmissivity and emissivity being in a frequency range corresponding to incident electromagnetic waves having millimeter or sub-millimeter wavelengths, said reflectivity, transmissivity and emissivity arising from incident electromagnetic waves falling incident on the area of interest and wherein the incident electromagnetic waves are produced from an extended source that is wider in dimensions than a dimension of a width of the area of interest under investigation and which extended source illuminates the area of interest from a wide angle with a first incoherent active source arranged to produce an illumination of the area under investigation in the observed frequency range, said illumination producing a contrast in detected power arising from reflectivity, transmissivity and/or emissivity in the presence of anomalies in or on the substrate or in or on or under the protective coating or layer, which contrast in the observed frequency range is different to one of (a) a detected power arising from naturally-occurring passive illumination of the substrate, protective coating or layer in the in situ environment in which the substrate or protective coating or layer is sited; and (b) a detected power emanating from the substrate or protective coating or layer in the in situ environment in which the substrate or protective coating or layer is sited;

identifying the presence of anomalies in the substrate by at least one of:
contrasting at least one of observed reflectivity, transmissivity and/or emissivity in adjacent areas of the substrate or the protective coating or layer applied to the substrate; and
contrasting at least one of observed reflectivity, transmissivity and/or emissivity of an area of the substrate or protecting layer or coating under investigation respectively against a reference reflectivity value, reference transmissivity value or reference emissivity anticipated for the area of the substrate under investigation.

2. The method of claim 1, further comprising:
determining emissivity from the substrate at two different temperatures to assess whether a change in emissivity has occurred between the two different temperatures; and
generating an output in the event that the change in emissivity exceeds a predetermined threshold, the output indicating the presence of at an anomaly in or on the substrate.

3. The method of claim 1, wherein the observed detected power is within at least one of frequency band in which atmospheric water and atmospheric oxygen are transparent to electromagnetic waves.

4. A detection system for identifying corrosion or anomalies in a substrate or in or under a protective layer or coating on the substrate, the detection system having:
an extended source arranged to generate incident electromagnetic waves;
an imaging system including a detector configured to receive and detect, in use, power emanating from an area of interest under investigation on or in the substrate or on or in or under the protective layer or coating;
a processor-based evaluation system responsive to the imaging system, the processor based evaluation system configured to present an indication of a difference in detected power;
wherein the detection system is configured to:
a) observe, in an observed frequency range, at least one of reflectivity, transmissivity and/or emissivity from the area of interest, said reflectivity, transmissivity and emissivity being in a frequency range corresponding to incident electromagnetic waves having millimeter or sub-millimeter wavelengths, said reflectivity, transmissivity and emissivity arising from incident electromagnetic waves falling incident on the area of interest;
and wherein the extended source is wider in dimensions than a dimension of a width of the area of interest under investigation and which extended source is arranged to illuminate the area of interest from a wide angle with a first incoherent active source configured to produce an illumination of the area under investigation in the observed frequency range, said illumination producing a contrast in detected power arising from reflectivity, transmissivity and/or emissivity in the presence of anomalies in or on or under the substrate or in or on the protective coating or layer, which contrast in the observed frequency range is different to one of (i) a detected power arising from naturally-occurring passive illumination of the substrate, protective coating or layer in the in situ environment in which the substrate or protective coating or layer is sited; and (ii) a detected power emanating from the substrate or protective coating or layer in the in situ environment in which the substrate or protective coating or layer is sited;
b) identify the presence of anomalies in or on the substrate or in, on or under the protective coating or layer by at least one of:
i) contrasting at least one of observed reflectivity, transmissivity and/or emissivity in adjacent areas of the substrate or the protective coating or layer applied to the substrate; and
ii) contrasting at least one of observed reflectivity, transmissivity and/or emissivity of an area of the substrate or protecting layer or coating under investigation respectively against a reference reflectivity value, reference transmissivity value or reference emissivity anticipated for the area of the substrate under investigation.

5. The detection system of claim 4, wherein the observed detected power is within at least one of frequency band in which atmospheric water and atmospheric oxygen are transparent to electromagnetic waves.

6. The detection system according to claim 4, wherein the processor-based evaluation system is further configured to provide an indication of confidence in structural integrity of the substrate under the layer applied over, or coating covering, the area under investigation on the substrate under investigation, the indication based on evaluating transmissivity through or emissivity of or the reflectivity from the layer or coating, the evaluation contrasting differences in the spectral profiles observed using the passive source and the active source.

7. The detection system according to claim 6, wherein the processor-based evaluation system is further configured to:
determine emissivity from the substrate at two different temperatures to assess whether a change in emissivity has occurred between the two different temperatures; and
generate an output in the event that the change in emissivity exceeds a predetermined threshold, the output indicating the presence of an anomaly in, on or under the layer applied to the substrate.

* * * * *